US011576412B2

(12) United States Patent
Lan et al.

(10) Patent No.: US 11,576,412 B2
(45) Date of Patent: Feb. 14, 2023

(54) EXTRACTS FROM FRUITS OF THE CUCURBITACEAE FAMILY, AND METHODS OF PREPARING THEREOF

(71) Applicant: Guilin GFS Monk Fruit Corporation, Guangxi (CN)

(72) Inventors: Fusheng Lan, Guangxi (CN); Jian Li, Guangxi (CN); Fengrui Wei, Guangxi (CN)

(73) Assignee: Guilin GFS Monk Fruit Corporation, Guangxi (CN)

( * ) Notice: Subject to any disclaimer, the term of this patent is extended or adjusted under 35 U.S.C. 154(b) by 847 days.

(21) Appl. No.: 16/312,229

(22) PCT Filed: Oct. 23, 2017

(86) PCT No.: PCT/CN2017/107363
§ 371 (c)(1),
(2) Date: Dec. 20, 2018

(87) PCT Pub. No.: WO2018/077140
PCT Pub. Date: May 3, 2018

(65) Prior Publication Data
US 2019/0230965 A1    Aug. 1, 2019

(30) Foreign Application Priority Data
Oct. 24, 2016  (WO) ................ PCT/CN2016/103078

(51) Int. Cl.
| A23L 27/12 | (2016.01) |
| A23L 27/30 | (2016.01) |
| A23L 2/04  | (2006.01) |
| A23L 2/74  | (2006.01) |
| A23L 2/08  | (2006.01) |
| A61K 36/42 | (2006.01) |
| A23L 2/10  | (2006.01) |

(52) U.S. Cl.
CPC ............ *A23L 27/12* (2016.08); *A23L 2/04* (2013.01); *A23L 2/08* (2013.01); *A23L 2/082* (2013.01); *A23L 2/102* (2013.01); *A23L 2/74* (2013.01); *A23L 27/36* (2016.08); *A61K 36/42* (2013.01); *A23V 2002/00* (2013.01); *A23V 2250/21* (2013.01); *A23V 2250/254* (2013.01); *A23V 2300/02* (2013.01); *A23V 2300/10* (2013.01); *A23V 2300/14* (2013.01); *A23V 2300/34* (2013.01); *A23V 2300/38* (2013.01); *A23V 2300/50* (2013.01)

(58) Field of Classification Search
CPC .......... A23L 27/12; A23L 27/36; A23L 2/082; A23L 2/74
See application file for complete search history.

(56) References Cited

U.S. PATENT DOCUMENTS

| 2,388,194 A | 10/1945 | Vallez |
| 2,926,110 A | 2/1960 | Hiroshi et al. |
| 3,437,491 A | 4/1969 | Peterson et al. |
| 4,775,541 A | 10/1988 | Brown et al. |
| 5,411,755 A | 5/1995 | Downton et al. |
| 5,419,251 A | 5/1995 | Mantius et al. |
| 5,433,965 A | 7/1995 | Fischer et al. |
| 5,679,806 A | 10/1997 | Zheng et al. |
| 6,124,442 A | 9/2000 | Zhou et al. |
| 6,461,659 B1 | 10/2002 | Zhou |
| 8,449,933 B2 | 5/2013 | Ekanayake et al. |
| 2003/0165603 A1 | 9/2003 | Burklow et al. |
| 2006/0003053 A1 | 1/2006 | Ekanayake et al. |
| 2008/0075824 A1 | 3/2008 | Biehl |
| 2008/0299277 A1 | 12/2008 | Chao et al. |
| 2009/0092690 A1 | 4/2009 | Yang et al. |
| 2009/0196966 A1 | 8/2009 | West et al. |
| 2009/0311404 A1 | 12/2009 | West et al. |
| 2010/0092638 A1* | 4/2010 | Hansen ................ A23L 27/33 426/548 |
| 2010/0285197 A1* | 11/2010 | Fisher .................. A23L 2/60 426/548 |
| 2011/0021456 A1 | 1/2011 | Lyndon et al. |
| 2011/0200712 A1 | 8/2011 | Takaichi |

(Continued)

FOREIGN PATENT DOCUMENTS

| CN | 87101850 A | 12/1987 |
| CN | 1015264 B | 1/1992 |

(Continued)

OTHER PUBLICATIONS

Search Report received for Chinese Patent Application No. 20178004792 dated Jan. 28, 2021, 6 pages (English translation pp. 1-3, Official copy pp. 4-6).
Advisory Action received for U.S. Appl. No. 12/310,517, dated May 16, 2014, 3 pages.
Aldrich, "Ion Exchange Resins: Classification and Properties", May 2018, pp. 28-30.
Brands et al., "Quantification of Melanoidin Concentration in Sugar-Casein Systems", Journal of Agricultural and Food Chemistry, vol. 50, No. 5, 2002, pp. 1178-1183.

(Continued)

*Primary Examiner* — Jeffrey P Mornhinweg
(74) *Attorney, Agent, or Firm* — Morrison & Foerster LLP

(57) ABSTRACT

The present disclosure relates to extracts and sweetening compositions that may be wholly derived from fruits of the Cucurbitaceae family containing mogroside V and other terpene glycosides. The extracts have a low mogroside V content. The extracts also have a low monosaccharide content, and can be spray-dried to form a spray-dried product. The extracts may be suitable for use as a bulking agent, and can be combined with a terpene glycoside powder. The extracts and sweetening compositions can be used in a food, beverage, and dietary supplement products. Provided are also methods for preparing such extracts and sweetening compositions.

10 Claims, 2 Drawing Sheets

(56) References Cited

U.S. PATENT DOCUMENTS

| | | | |
|---|---|---|---|
| 2014/0044843 | A1 | 2/2014 | Lyndon |
| 2015/0216209 | A1 | 8/2015 | Lyndon et al. |
| 2016/0235098 | A1* | 8/2016 | Cox .................. A23G 3/38 |
| 2018/0000140 | A1 | 1/2018 | Lyndon |
| 2020/0138063 | A1 | 5/2020 | Lyndon et al. |
| 2021/0282440 | A1 | 9/2021 | Lyndon |

FOREIGN PATENT DOCUMENTS

| | | |
|---|---|---|
| CN | 1019935 C | 2/1993 |
| CN | 1244531 A | 2/2000 |
| CN | 1259519 A | 7/2000 |
| CN | 1375499 A | 10/2002 |
| CN | 1508139 A | 6/2004 |
| CN | 1556110 A | 12/2004 |
| CN | 1600179 A | 3/2005 |
| CN | 1618335 A | 5/2005 |
| CN | 1620883 A | 6/2005 |
| CN | 1634814 A | 7/2005 |
| CN | 1663469 A | 9/2005 |
| CN | 1663474 A | 9/2005 |
| CN | 1683387 A | 10/2005 |
| CN | 1706861 A | 12/2005 |
| CN | 1723981 A | 1/2006 |
| CN | 1733130 A | 2/2006 |
| CN | 1733754 A | 2/2006 |
| CN | 1733785 A | 2/2006 |
| CN | 1733795 A | 2/2006 |
| CN | 1854149 A | 11/2006 |
| CN | 1872133 A | 12/2006 |
| CN | 1907091 A | 2/2007 |
| CN | 1303914 C | 3/2007 |
| CN | 101006849 A | 8/2007 |
| CN | 101007042 A | 8/2007 |
| CN | 100336822 C | 9/2007 |
| CN | 101029088 A | 9/2007 |
| CN | 101054384 A | 10/2007 |
| CN | 101057878 A | 10/2007 |
| CN | 100348610 C | 11/2007 |
| CN | 101096693 A | 1/2008 |
| CN | 101104628 A | 1/2008 |
| CN | 100382723 C | 4/2008 |
| CN | 101182286 A | 5/2008 |
| CN | 100391495 C | 6/2008 |
| CN | 101200753 A | 6/2008 |
| CN | 101228843 A | 7/2008 |
| CN | 100425605 C | 10/2008 |
| CN | 101283764 A | 10/2008 |
| CN | 101283831 A | 10/2008 |
| CN | 101285027 A | 10/2008 |
| CN | 101386636 A | 3/2009 |
| CN | 101402665 A | 4/2009 |
| CN | 101407535 A | 4/2009 |
| CN | 100491381 C | 5/2009 |
| CN | 101433592 A | 5/2009 |
| CN | 101434608 A | 5/2009 |
| CN | 101434636 A | 5/2009 |
| CN | 100513426 C | 7/2009 |
| CN | 101502313 A | 8/2009 |
| CN | 101522058 A | 9/2009 |
| CN | 100572552 C | 12/2009 |
| CN | 100589813 C | 2/2010 |
| CN | 101096693 B | 4/2010 |
| CN | 101690573 A | 4/2010 |
| CN | 101006849 B | 5/2010 |
| CN | 101007042 B | 5/2010 |
| CN | 101708249 A | 5/2010 |
| CN | 101711823 A | 5/2010 |
| CN | 101816790 A | 9/2010 |
| CN | 101120653 B | 10/2010 |
| CN | 101228843 B | 10/2010 |
| CN | 101708249 B | 10/2010 |
| CN | 101402665 B | 12/2010 |
| CN | 101711823 B | 12/2010 |
| CN | 101946887 A | 1/2011 |
| CN | 101948340 A | 1/2011 |
| CN | 101948501 A | 1/2011 |
| CN | 101973853 A | 2/2011 |
| CN | 101434608 B | 4/2011 |
| CN | 101386636 B | 5/2011 |
| CN | 101407535 B | 5/2011 |
| CN | 102048791 A | 5/2011 |
| CN | 102048857 A | 5/2011 |
| CN | 102050707 A | 5/2011 |
| CN | 102050848 A | 5/2011 |
| CN | 102058727 A | 5/2011 |
| CN | 101249130 B | 6/2011 |
| CN | 101433592 B | 6/2011 |
| CN | 101434636 B | 6/2011 |
| CN | 102084982 A | 6/2011 |
| CN | 102100394 A | 6/2011 |
| CN | 102125248 A | 7/2011 |
| CN | 102125249 A | 7/2011 |
| CN | 102180913 A | 9/2011 |
| CN | 102742801 A | 10/2012 |
| CN | 103145869 A | 6/2013 |
| CN | 103652776 A | 3/2014 |
| CN | 104086614 A | 10/2014 |
| CN | 104530168 A | 4/2015 |
| CN | 104558088 A | 4/2015 |
| CN | 106028835 A | 10/2016 |
| EP | 0229520 A1 | 7/1987 |
| EP | 2090181 A1 | 8/2009 |
| EP | 2190854 B1 | 11/2011 |
| EP | 2397485 A1 | 12/2011 |
| EP | 2882301 B1 | 9/2016 |
| JP | 56-158072 A | 12/1981 |
| JP | 58-71868 A | 4/1983 |
| JP | 9-234016 A | 9/1997 |
| JP | 2001-211854 A | 8/2001 |
| JP | 2010-502213 A | 1/2010 |
| JP | 2014-36678 A | 2/2014 |
| WO | 2006/005011 A1 | 1/2006 |
| WO | 2008/030121 A1 | 3/2008 |
| WO | 2008/102137 A1 | 8/2008 |
| WO | 2008/129457 A1 | 10/2008 |
| WO | 2009/038978 A2 | 3/2009 |
| WO | 2011/066754 A1 | 6/2011 |
| WO | WO-2012088169 A1 | 6/2012 |
| WO | 2018/077140 A1 | 5/2018 |

OTHER PUBLICATIONS

Davis, SB, "The Chemistry of Colour Removal: A Processing Perspective", Proc S Afr Sug Technol Ass, vol. 75, 2001, pp. 328-336.
"Dow Liquid Separations. DOWEX Ion Exchange Resins. Juice Enhancement by Ion Exchange and Adsorbent Technologies.", Edited by: P. R. Ashurst, 7 pages.
Extended European Search Report received for European Patent Application No. 16189800.2, dated Dec. 16, 2016, 5 pages.
Final Office Action received for U.S. Appl. No. 12/310,517, dated Dec. 11, 2015, 19 pages.
Final Office Action received for U.S. Appl. No. 12/310,517, dated Mar. 11, 2014, 9 pages.
Final Office Action received for U.S. Appl. No. 13/961,763, dated Aug. 18, 2016, 12 pages.
Final Office Action received for U.S. Appl. No. 13/961,763, dated Oct. 8, 2014, 10 pages.
Final Office Action received for U.S. Appl. No. 14/685,507, dated May 18, 2018, 14 pages.
Final Office Action received for U.S. Appl. No. 14/685,507, dated Oct. 11, 2019, 11 pages.
Final Office Action received for U.S. Appl. No. 15/434,834, dated Sep. 23, 2019, 12 pages.
Galletti, Carl J., "Just the Facts: Knowing Strong Base Anion Resin Types", Available online at <https://www.wwdmag.com/just-facts-knowing-strong-base-anion-resin-types>, Dec. 28, 2000, 4 pages.
Harland, C E., "Ion Exchange Theory and Practice", 2nd Edition, Royal Society of Chemistry, 1994, pp. 59 and 63.

(56) References Cited

OTHER PUBLICATIONS

International Preliminary Report on Patentability received for PCT Patent Application No. PCT/CN2017/107363, dated May 9, 2019, 5 pages.
International Preliminary Report on Patentability received for PCT Patent Application No. PCT/NZ2007/000263, completed on Dec. 11, 2008, 11 pages.
International Preliminary Report on Patentability received for PCT Patent Application No. PCT/US2013/054007, dated Feb. 19, 2015, 6 pages.
International Search Report and Written Opinion received for PCT Patent Application No. PCT/CN2017/107363, dated Jan. 18, 2018, 6 pages.
International Search Report and Written Opinion received for PCT Patent Application No. PCT/NZ2007/000263, dated Jan. 15, 2008, 10 pages.
International Search Report received for PCT Patent Application No. PCT/US2013/054007, dated Sep. 26, 2013, 3 pages.
International Written Opinion received for PCT Patent Application No. PCT/US2013/054007, dated Sep. 26, 2013, 5 pages.
Lee, Chi-Hang, "Intense sweetener from Lo Han Kuo (Momordica grosvenori)", Experientia, vol. 31, No. 5, Oct. 17, 1974, pp. 533-534.
Liu, Zhongdong, "Extraction and Purification of Mogroside (V)", Ion Exchange and Adsorption, vol. 15, No. 4, 1999, pp. 364-368 (With English Abstract).
Madhavan, R., "Optimization Liquid-Liquid Extraction", Chemical Engineering Tools and Information, Feb. 2001, pp. 1-12.
Matsumoto et al., "Minor Cucurbitane-Glycosides from Fruits of Siraitia grosvenori (Cucurbitaceae)", Chemical and Pharmaceutical Bulletin, vol. 38, No. 7, 1990, pp. 2030-2032.
Morris, Manning & Martin, LLP, "Explanation of Qin Benjun, et al and Yu Lijuan et al Documents", pp. 1-13.
Non-Final Office Action received for U.S. Appl. No. 12/310,517, dated Jul. 3, 2012, 8 pages.
Final Office Action received for U.S. Appl. No. 15/434,834, dated Sep. 23, 2013, 8 pages.
Non-Final Office Action received for U.S. Appl. No. 13/961,763, dated Feb. 10, 2014, 14 pages.
Non-Final Office Action received for U.S. Appl. No. 13/961,763, dated Jan. 12, 2016, 11 pages.
Non-Final Office Action received for U.S. Appl. No. 15/434,834, dated Jan. 18, 2019, 11 pages.
Non-Final Office Action received for U.S. Appl. No. 12/310,517, dated Jan. 13, 2015, 9 pages.
Non-Final Office Action received for U.S. Appl. No. 14/685,507, dated Aug. 15, 2017, 12 pages.
Non-Final Office Action received for U.S. Appl. No. 14/685,507, dated Dec. 13, 2016, 15 pages.
Norit, "Norit Novelties in Sugar & Sweetener Purification", Know How Magazine, No. 1, 2005, pp. 1-2.
Puretec, "Basics of Deionized Water by Ion Exchange", Available Online at <https://puretecwater.com/downloads/basics-of-ion-exchange.pdf>, 2 pages.
Rohm and Haas, "Ion Exchange for Dummies", Available online at <http://www.lenntech.com/Data-sheets/Ion-Exchange-for-Dummies-RH.pdf>, Sep. 2008, pp. 1-9.
Extended European Search Report received for European Patent Application No. 07834865.3, dated Jun. 10, 2010, 8 pages.
Takemoto et al., "Studies on the Constituents of Fructus Momordicae. III. Structure of Mogrosides", Yakugaku Zasshi, vol. 103, No. 11, 1983, pp. 1167-1173 (With English Abstract).
Tang et al., "Chemical Constituents of Momordica Grosvenori", Chinese Drugs of Plant Origin: Chemistry, Pharmacology, and Use in Traditional and Modern Medicine, vol. 21, No. 6, 1992, 2 pages.
Wheaton et al., "Fundamentals of Ion Exchange", Dowex Ion Exchange Resins, Jun. 2000, 9 pages.
Yoshikawa et al., "Transglycosylation of Mogroside V, A Triterpene Glycoside in Siraitia Grosvenori, by Cyclodextrin Glucanotransferase and Improvement of the Qualities of Sweetness", J. Appl. Glycosci., vol. 52, 2005, pp. 247-252.
Yu et al., "Preparation of Mogroside V from Fresh Fruits of Luohanguo by High Performance Liquid chromatography", Chinese Journal of Chromatography, vol. 21, No. 4, Jul. 2003, pp. 397-399 (With English Abstract).
Extended European Search Report received for European Patent Application No. 17863694.0, dated May 6, 2020, 9 Pages.
Yu et al., (2014). "Chapter 12: Saccharides," Medical Chemistry, Huazhong University of Science & Technology Press, p. 123, 4 pages.

* cited by examiner

EXTRACTS FROM FRUITS OF THE CUCURBITACEAE FAMILY, AND METHODS OF PREPARING THEREOF

CROSS-REFERENCE TO RELATED APPLICATIONS

This application is a National Phase application under 35 U.S.C. § 371 of International Application No. PCT/CN2017/107363, filed Oct. 23, 2017, which claims priority to PCT/CN2016/103078, filed Oct. 24, 2016, each of which is incorporated herein by reference in their entirety.

FIELD

The present disclosure relates generally to extracts from terpene-glycoside containing fruits of the family Cucurbitaceae, and more specifically, the present disclosure relates to extracts derived from luo han guo that may be suitable for use as bulking agents and methods of preparing and using thereof.

BACKGROUND

Various methods are known in the art to produce sweetening compositions from luo han guo. However, such sweetening compositions typically use maltodextrin as a bulking agent in the commercial product. Thus, there is a need in the art to produce bulking agents from luo han guo, so as to produce an all-natural sweetening composition derived from the fruit.

BRIEF SUMMARY

In some aspects, provided is a luo han guo extract, comprising: mogroside V, monosaccharides, disaccharides, and proteins, wherein the extract has less than about 1% mogroside V on a dry weight basis and less than about 20% monosaccharides on a dry weight basis, and wherein the mogroside V, monosaccharides, disaccharides, and proteins are all naturally occurring in luo han guo.

In other aspects, provided is a method of producing a spray-dried extract, comprising:

a) filtering a mogroside-depleted luo han guo juice using a nanofiltration membrane to produce a retentate, wherein the nanofiltration membrane has a molecular weight cut-off between 200 Daltons and 2,500 Daltons;

b) monitoring the soluble solids concentration of the retentate of step (a);

c) diluting the retentate of step (a) with water, when the soluble solids concentration of the retentate of step (a) is about 5 g/100 g, to produce a diluted retentate;

d) filtering the diluted retentate using the nanofiltration membrane to produce another retentate;

e) monitoring the soluble solids concentration of the retentate of step (d);

f) diluting the retentate of step (d) with water to produce another diluted retentate;

g) repeating steps (d)-(f) until the monosaccharide concentration of the retentate of step (d) is less than about 20% on a dry weight basis;

h) after step (g), concentrating the retentate to produce a concentrated retentate having a soluble solids concentration of about 20 g/100 g; and i) spray drying the concentrated retentate to produce the spray-dried extract.

In one variation, provided is a method of producing a luo han guo sweetening composition, comprising:

a) heating fresh luo han guo in water to obtain a water-extracted juice, wherein the water-extracted juice comprises mogroside V and other terpene glycosides;

b) clarifying the water-extracted juice, wherein the clarified juice comprises mogroside V and other terpene glycosides;

c) contacting the clarified juice with an absorbent resin, wherein at least a portion of the mogroside V and other terpene glycosides in the clarified juices binds to the adsorbent resin to produce a mogroside-depleted juice;

d) after step c), eluting the mogroside V and other terpene glycosides from the adsorbent resin to obtain a terpene glycoside solution;

e) drying the terpene glycoside solution to produce a terpene glycoside powder;

f) filtering the mogroside-depleted juice using a nanofiltration membrane to produce a retentate, wherein the nanofiltration membrane has a molecular weight cut-off between 200 and 2,500 Daltons;

g) monitoring the soluble solids concentration of the retentate of step (f);

h) diluting the retentate of step (f) with water, when the soluble solids concentration of the retentate of step (f) is about 5 g/100 g, to produce a diluted retentate;

i) filtering the diluted retentate using the nanofiltration membrane to produce another retentate;

j) monitoring the soluble solids concentration of the retentate of step (i);

k) diluting the retentate of step (i) with water to produce another diluted retentate;

l) repeating steps (f)-(k) until the monosaccharide concentration of the retentate of step (i) is about 20% on a dry weight basis;

m) after step (l), concentrating the retentate to produce a concentrated retentate having a soluble solids concentration of about 20 g/100 g;

n) spray drying the concentrated retentate to produce the spray-dried extract; and o) combining the terpene glycoside powder and the spray-dried extract to produce the sweetening composition, wherein the sweetening composition is in solid form.

In another variation, provided is a method of producing a luo han guo sweetening composition, comprising:

a) heating fresh luo han guo in water to obtain a water-extracted juice, wherein the water-extracted juice comprises mogroside V and other terpene glycosides;

b) clarifying the water-extracted juice, wherein the clarified juice comprises mogroside V and other terpene glycosides;

c) contacting the clarified juice with an absorbent resin, wherein at least a portion of the mogroside V and other terpene glycosides in the clarified juices binds to the adsorbent resin to produce a mogroside-depleted juice;

d) after step c), eluting the mogroside V and other terpene glycosides from the adsorbent resin to obtain a terpene glycoside solution;

e) drying the terpene glycoside solution to produce a terpene glycoside powder;

f) filtering the mogroside-depleted juice using a nanofiltration membrane to produce a retentate, wherein the nanofiltration membrane has a molecular weight cut-off between 200 and 2,500 Daltons;

g) monitoring the soluble solids concentration of the retentate of step (f);

h) diluting the retentate of step (f) with water, when the soluble solids concentration of the retentate of step (f) is about 5 g/100 g, to produce a diluted retentate;

i) filtering the diluted retentate using the nanofiltration membrane to produce another retentate;

j) monitoring the soluble solids concentration of the retentate of step (i);

k) diluting the retentate of step (i) with water to produce another diluted retentate;

l) repeating steps (f)-(k) until the monosaccharide concentration of the retentate of step (i) is about 20% on a dry weight basis;

m) after step (l), concentrating the retentate to produce a concentrated retentate having a soluble solids concentration of about 20 g/100 g;

n) combining the concentrated retentate of step (m) with the terpene glycoside powder of step (e); and o) spray drying the combined concentrated retentate and terpene glycoside powder to produce the luo han guo sweetening composition.

In some aspects, provided herein are also luo han guo sweetening compositions produced according to any one of the methods described herein. In other aspects, provided is a food, beverage, or dietary supplement product comprising any of the extracts or the sweetening compositions described herein.

DESCRIPTION OF THE FIGURES

The present application can be understood by reference to the following description taken in conjunction with the accompanying figures.

DETAILED DESCRIPTION

Figure 1:
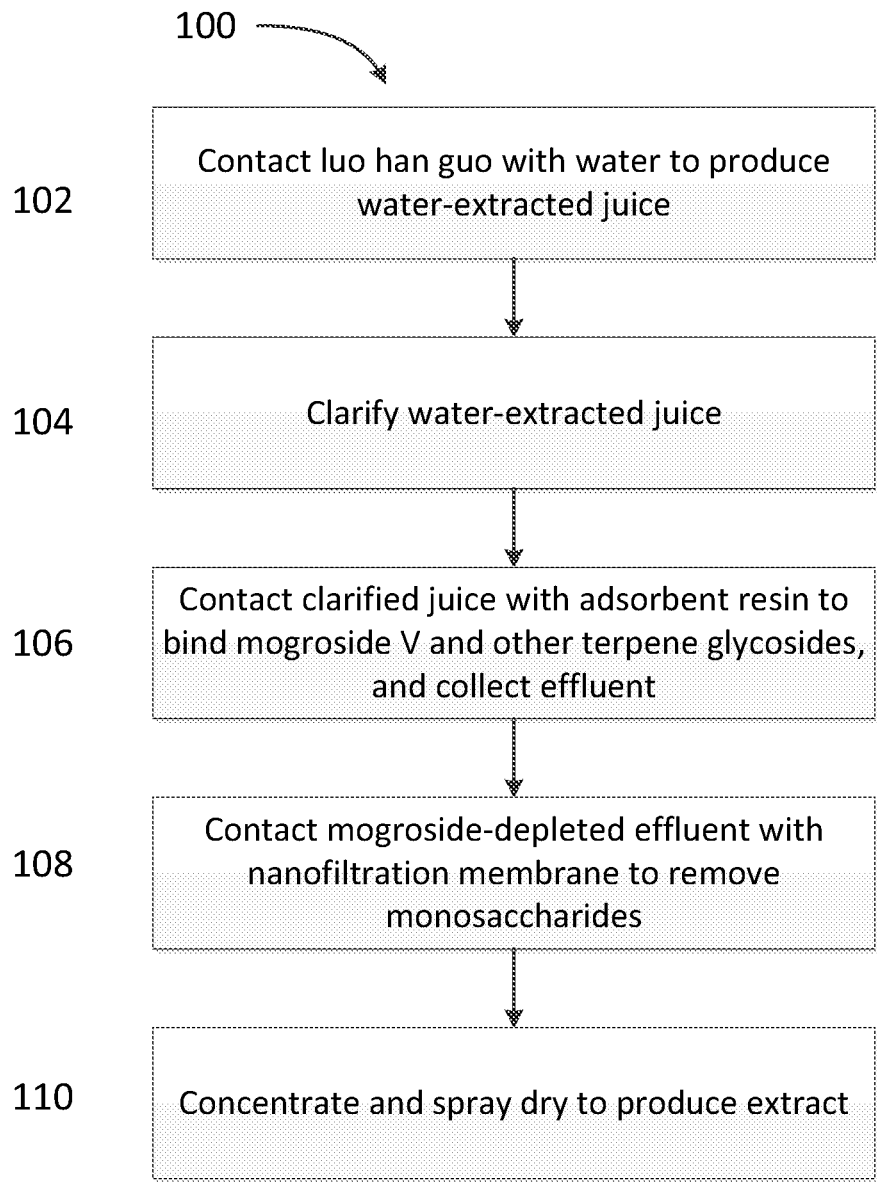
FIG. 1 depicts an exemplary process to prepare a luo han guo extract having a low mogroside V content and a low monosaccharide content.

The following description sets forth exemplary methods, parameters and the like. It should be recognized, however, that such description is not intended as a limitation on the scope of the present disclosure but is instead provided as a description of exemplary embodiments.

Provided herein are extracts obtained from terpene glycoside-containing fruits of the Cucurbitaceae, and methods of producing and using such extracts. In particular, the fruits of the family Cucurbitaceae family contain at least one particular terpene glycoside, mogroside V. In some variations, the fruit of the Cucurbitaceae family is monk fruit, also known in the art by its Chinese name, luo han guo (*Siraitia grosvenorii*, formerly known as *Momordica grosvenorii*).

In some aspects, provided is a luo han guo extract comprising a low mogroside V content, and if monosaccharides are present in the extract, a low monosaccharide content. The low monosaccharide content allows for spray drying to produce the extract in powder form. Thus, in some variations, the extract is in powder form. Such extract in powder form may be suitable for use as a bulking agent in preparing a sweetening composition. For example, the extract in powder form may be combined with a terpene-glycoside composition to produce a sweetening composition. Such sweetening composition may be in solid form. For example, such sweetening composition may combine the extract and terpene-glycoside composition in powder form, or the extract and terpene-glycoside composition may be compressed into a tablet.

By incorporating the extracts described herein as a bulking agent in sweetening compositions, the sweetening compositions have a low overall mogroside V content, with components that may all be derived from the fruit from which the extracts were obtained.

Provided herein are also methods for producing the extracts described herein, as well as methods for producing the sweetening composition that incorporates such extracts as a bulking agent.

The extracts and the sweetening compositions incorporating such extracts, as well as methods for producing thereof, are described in further detail below.

Extract

In some aspects, provided is a luo han guo extract comprising mogroside V. In some variations, the extract has less than about 20% on a dry weight basis of monosaccharides, if present in the extract. The mogroside V and monosaccharides, if present, are all naturally occurring in the luo han guo from which the extract was obtained.

In addition to mogroside V and, if present, monosaccharides, the extracts described herein further comprise additional components that are naturally occurring in luo han guo from which the extracts are obtained. Such additional naturally-occurring components may include, for example, disaccharides, polysaccharides, proteins, other terpene glycosides, fruit acids, and minerals.

In some variations, at least 95%, at least 96%, at least 97%, at least 98%, at least 99%, at least 99.5%, or at least 99.9% of the components in the extract, on a dry weight basis, are naturally occurring (or naturally present) in luo han guo from which the extract was obtained. In certain variations, all components of the extract are naturally occurring (or naturally present) in luo han guo from which the extract was obtained. Thus, in certain variations, the extract is a natural luo han guo extract. In one variation, a natural luo han guo extract may include less than 5%, less than 4%, less than 3%, less than 2%, or less than 1% on a dry weight basis of an incidental additive or processing aid that is not naturally occurring (or naturally present) in luo han guo. In one variation, a natural luo han guo extract may include a trace amount or less than 0.01% on a dry weight basis of a non-naturally occurring component.

Mogroside V

Mogroside V is a terpene glycoside, whose chemical structure is known in the art. In some embodiments, the extract has less than or equal to about 3%, less than or equal to about 2.5%, less than or equal to about 2%, less than or equal to about 1.5%, less than or equal to about 1%, less than or equal to about 0.95%, less than or equal to about 0.9%, less than or equal to about 0.85%, less than or equal to about 0.8%, less than or equal to about 0.75%, less than or equal to about 0.7%, less than or equal to about 0.65%, less than or equal to about 0.6%, less than or equal to about 0.55%, less than or equal to about 0.5%, less than or equal to about 0.4%, less than or equal to about 0.3%, less than or equal to about 0.2%, or less than or equal to about 0.1% mogroside V on a dry weight basis.

In other embodiments, the extract has between about 0.001% and about 2.5%, between about 0.01% and about 2.5%, between about 0.1% and about 2.5%, between about 0.5% and about 2.5%, between about 1% and about 2.5%, between about 0.001% and about 2%, between about 0.01% and about 2%, between about 0.1% and about 2%, between about 0.5% and about 2%, between about 1% and about 2%, between about 0.001% and about 1.5%, between about 0.01% and about 1.5%, between about 0.1% and about 1.5%, between about 0.5% and about 1.5%, between about 0.001% and about 1%, between about 0.01% and about 1%, between about 0.1% and about 1%, between about 0.5% and about 1% mogroside V on a dry weight basis.

It should be understood that the amounts of mogroside V in the extract are expressed as a percentage based on a dry weight basis of the extract. In some variations of the foregoing, the amount of mogroside V in the extract is determined by high-performance liquid chromatography (HPLC). It should also generally be understood that the mogroside V content in the extract may be determined by any suitable methods or techniques known in the art.

The mogroside V in the extract is naturally occurring in the luo han guo from which the extract is obtained. In some variations, the extract has an amount of mogroside V less than or equal to the amount of mogroside V naturally occurring in luo han guo from which the extract is obtained. In certain variations, the extract has an amount of mogroside V less than the amount of mogroside V naturally occurring in luo han guo from which the extract is obtained. In one variation, the extract has an amount of mogroside V that is two times less, three times less, or four times less than the amount of mogroside V naturally occurring in luo han guo from which the extract is obtained. In another variation, the extract has an amount of mogroside V that is between two to three times less, three to four times less, or two to four times less than the amount of mogroside V naturally occurring in luo han guo from which the extract is obtained.

Monosaccharides

In some embodiments, the extract has less than or equal to about 20%, less than or equal to about 19%, less than or equal to about 18%, less than or equal to about 17%, less than or equal to about 16%, less than or equal to about 15%, less than or equal to about 14%, less than or equal to about 13%, less than or equal to about 12%, less than or equal to about 11%, less than or equal to about 10%, less than or equal to about 9%, less than or equal to about 8%, less than or equal to about 7%, less than or equal to about 6%, less than or equal to about 5%, less than or equal to about 4%, less than or equal to about 3%, less than or equal to about 2%, of less than or equal to about 1% monosaccharides on a dry weight basis.

In other embodiments, the extract has between about 1% and about 20%, between about 5% and about 20%, between about 10% and about 20%, between about 1% and about 18%, between about 5% and about 18%, between about 10% and about 18%, between about 1% and about 16%, between about 5% and about 16%, between about 10% and about 16%, between about 1% and about 14%, between about 5% and about 14%, between about 10% and about 14%, between about 1% and about 12%, between about 5% and about 12%, or between about 10% and about 12% monosaccharides on a dry weight basis.

It should be understood that the amounts of monosaccharides in the extract are expressed as a percentage based on a dry weight basis of the extract. In some variations of the foregoing, the amount of monosaccharides in the extract is determined by high-performance liquid chromatography-refractive index detector (HPLC-RID). It should also generally be understood that the monosaccharide content in the extract may be determined by any suitable methods or techniques known in the art.

The monosaccharides in the extract are naturally occurring in the luo han guo from which the extract is obtained. Such monosaccharides may include, for example, glucose and fructose. In some variations, the extract has an amount of monosaccharides less than or equal to the amount of monosaccharides naturally occurring in luo han guo from which the extract is obtained. In certain variations, the extract has an amount of monosaccharides less than the amount of monosaccharides naturally occurring in luo han guo from which the extract is obtained. In one variation, the extract has an amount of monosaccharides that is two times less, three times less, four times less, five times less, or six times less than the amount of monosaccharides naturally occurring in luo han guo from which the extract is obtained. In another variation, the extract has an amount of monosaccharides that is between two to three times less, between three to four times less, between four to five times less, between two to four times less, between two to five times less, or between three to five times less than the amount of monosaccharides naturally occurring in luo han guo from which the extract is obtained.

It should also be understood that any of the variations of the mogroside V content and the monosaccharide content described herein may be combined as if each and every combination were individually listed. For example, in one variation, the extract has less than or equal to about 1% mogroside V on a dry weight basis and less than about 20% monosaccharides on a dry weight basis. In another variation, the extract has less than or equal to about 0.5% mogroside V on a dry weight basis and less than or equal to about 12% monosaccharides on a dry weight basis.

Disaccharides

In some embodiments, the extract further comprises disaccharides naturally occurring in luo han guo from which the extract is obtained. Such disaccharides may include, for example, sucrose.

In some variations, the extract has at least 25%, at least 30%, at least 40%, or at least 50% disaccharides on a dry weight basis. It should be understood that the amounts of disaccharides in the extract are expressed as a percentage based on a dry weight basis of the extract. In some variations of the foregoing, the amount of disaccharides in the extract is determined by high-performance liquid chromatography-refractive index detector (HPLC-RID). It should also generally be understood that the disaccharide content in the extract may be determined by any suitable methods or techniques known in the art.

In some variations, the amount of disaccharides in the extract may be expressed relative to the amount of monosaccharides therein. For example, in certain variations, the weight ratio of monosaccharides to disaccharides in the extract, on a dry weight basis, is less than or equal to about 0.5:1, less than or equal to about 0.45:1, less than or equal to about 0.4:1, less than or equal to about 0.35:1, less than or equal to about 0.3:1, less than or equal to about 0.2:1, or less than or equal to about 0.1:1. In other variations, the weight ratio of monosaccharides to disaccharides in the extract, on a dry weight basis, is between about 0.5:1 and about 0.25:1, between about 0.25:1 and about 0.1:1, or between about 0.5:1 and about 0.1:1.

It should also be understood that any of the variations of disaccharide content may be combined with the variations of the mogroside V content and the monosaccharide content described herein, as if each and every combination were individually listed. For example, in one variation, the extract comprises mogroside V, monosaccharides and disaccharides, wherein the extract has less than or equal to about 1% mogroside V on a dry weight basis and less than or equal to about 20% monosaccharides on a dry weight basis, and wherein the weight ratio of monosaccharides to disaccharides in the extract, on a dry weight basis, is less than or equal to about 0.5:1.

Proteins

In some embodiments, the extract further comprises proteins, or fragments or derivatives thereof, naturally occurring in luo han guo from which the extract is obtained. In some variations, the extract has at least about 10%, at least about 11%, at least about 12%, at least about 13%, at least about 14%, at least about 15%, at least about 16%, at least about 17%, or at least about 18% proteins, or fragments or derivatives thereof, on a dry weight basis. In certain variations, the amount of proteins, or fragments or derivatives thereof, in the extract, on a dry weight basis, does not exceed about 18%, about 17%, about 16%, or about 15%. In other variations, the extract has between about 10% and about 18%, between about 12% and about 18%, between about 14% and about 18%, between about 10% and about 16%, between about 12% and about 16%, between about 14% and about 16%, between about 10% and about 14%, or between about 12% and about 14% proteins, or fragments or derivatives thereof, on a dry weight basis.

It should be understood that the amounts of proteins, or fragments or derivatives thereof, in the extract are expressed as a percentage based on a dry weight basis of the extract. In some variations of the foregoing, the amount of proteins, or fragments or derivatives thereof, in the extract is determined by Kjeldahl Nitrogen Method. It should also generally be understood that the content of proteins, or fragments or derivatives thereof, in the extract may be determined by any suitable methods or techniques known in the art.

It should also be understood that any of the variations of protein (or fragments or derivatives thereof) content may be combined with the variations of the mogroside V content, the monosaccharide content, and the disaccharide content described herein, as if each and every combination were individually listed. For example, in one variation, the extract comprises mogroside V, monosaccharides, disaccharides and proteins (or fragments or derivatives thereof), wherein the total amount of mogroside V in the extract does not exceed about 0.6% on a dry weight basis, wherein the extract has less than about 20% monosaccharides on a dry weight basis, wherein the weight ratio of monosaccharides to disaccharides in the extract, on a dry weight basis, is less than or equal to about 0.5:1, and wherein the extract has between about 10% and 18% proteins, or fragments or derivatives thereof, on a dry weight basis.

Fruit Acids

In some embodiments, the extract further comprises fruit acids naturally occurring in luo han guo from which the extract is obtained. Such naturally-occurring fruit acids may include, for example, ascorbic acid, citric acid and lactic acid.

In some variations, the extract has a total acid content less than about 5%, less than about 4%, less than about 3%, less than about 2.5%, less than about 2%, less than about 1.5%, or less than about 1% on a dry weight basis. It should be understood that the total acid content of the extract is expressed as a percentage based on a dry weight basis of the extract. In one variation, the total acid content is determined by titratable acidity, measured based on citric acid.

In other variations, the extract has a total acid content less than or equal to two times less, three times less, four times less, or five times less than the total acid content naturally occurring in luo han guo from which the extract is obtained.

Other Components

In some embodiments, the extract further comprises other terpene glycosides (i.e., terpene glycosides other than mogroside V) that are naturally occurring in luo han guo from which the extract is obtained. Such terpene glycosides include other mogrosides and siamenosides. Other mogrosides may include, for example, mogrosides I, II, III, IV and VI, whose chemical structure is known in the art. In some embodiments, the extract has a weight ratio of mogroside V to the other terpene glycosides, on a dry weight basis, that is similar to or the same as the weight ratio in luo han guo from which the extract is obtained.

In some embodiments, the extract further comprises polysaccharides naturally occurring in luo han guo from which the extract is obtained. It should generally be understood that the polysaccharide content in the extract may be determined by any suitable methods or techniques known in the art. In some variations, the extracts described herein contain monosaccharides, disaccharides and polysaccharides. It should be understood that the extracts described herein have a total sugar content, wherein the total sugar content is the sum of the monosaccharide, disaccharide and polysaccharide amounts in the extract, on a dry weight basis. In some embodiments, the amount of monosaccharides, disaccharides and polysaccharides present in the extract may be expressed relative to the total sugar content. For example, in some variations, the extract has an amount of monosaccharide less than or equal to about 25%, less than or equal to about 20%, less than or equal to about 15%, less than or equal to about 10%, or less than or equal to about 5% by weight of the total sugars in the extract. In other variations, the extract has an amount of monosaccharide between about 5% and about 25%, between about 10% and about 25%, between about 15% and about 25%, between about 5% and about 20%, between about 10% and about 20%, or between about 15% and about 20% by weight of the total sugar content in the extract. In yet other variations, the weight ratio of monosaccharides to the total sugar content in the extract is two times less, three times less, four times less, between two to three times less, between two to four times less, or between three to four times less than the weight ratio of monosaccharides to the total sugar content of luo han guo from which the extract is obtained.

The extracts may further comprise additional flavor and color components that are naturally occurring in luo han guo from which the extract is obtained. In some variations, the additional flavor and color components may include, for example, polyphenolic compounds and/or melanoidin compounds. In certain variations, the extracts have a lower amount of polyphenolic compounds than the amount of polyphenolic compounds in luo han guo from which the extract is obtained.

Methods for Producing the Extract

In other aspects, provided herein are methods for producing extracts derived from a fruit of the family Cucurbitaceae, such as luo han guo, wherein the extracts have a low mogroside V content and a low monosaccharide content. In some variations, the fruit is luo han guo. In one variation, the luo han guo has at least 1% w/w of mogroside V.

In some embodiments, provided is a method for producing the extract that comprises extracting a juice from luo han guo, contacting the extracted juice with an adsorbent medium to lower the mogroside V content, and then contacting the extracted juice with a nanofiltration membrane to lower the monosaccharide content. In such an embodiment, the extracted juice is contacted with the adsorbent medium prior to the nanofiltration step. Such adsorbent medium may be an adsorbent resin. In other embodiments, other methods suitable for reducing the mogroside V content may be employed.

With reference to FIG. 1, process 100 is an exemplary process to prepare an extract having a low mogroside V content and a low monosaccharide content. In step 102, the fruit is contacted with water to produce a water-extracted juice. The water-extracted juice comprises mogroside V, other terpene glycosides and monosaccharides. The water-extracted juice is clarified in step 104 (e.g., to remove pectin and other proteins), thereby facilitating subsequent processing. In step 106, the clarified juice is contacted with an adsorbent resin, wherein at least a portion of the mogroside V and other terpene glycosides in the clarified juice are adsorbed onto the resin. The effluent that comes off the adsorbent resin is a mogroside-depleted effluent, and is contacted with a nanofiltration membrane in step 108. At least a portion of small molecules, including monosaccharides and fruit acids, are removed in step 108. In step 110, the retentate produced from the nanofiltration step is concentrated and spray-dried to produce an extract.

It should be understood that, in other variations, process 100 may include additional processing steps. In yet other variations, certain steps in process 100 may be omitted.

In one variation, provided is method for producing an extract derived from a fruit of the Cucurbitaceae family, the method comprising:

contacting the fruit with water to obtain a water-extracted juice, wherein the water-extracted juice comprises mogroside V and monosaccharides;

clarifying the water-extracted juice;

contacting the clarified juice with an adsorbent medium to adsorb at least a portion of mogroside V in the clarified juice and to produce an effluent;

filtering the effluent using a nanofiltration membrane to remove at least a portion of the monosaccharides in the effluent and to produce a retentate; and concentrating and spray drying the retentate to produce the extract.

The extract obtained after spray drying is in powder form. The extract obtained from the method above has a low mogroside V content and a low monosaccharide content.

The effluent obtained from contact with the adsorbent medium has a lower mogroside V content, as well as a lower overall terpene glycoside content, than the mogroside V and overall terpene glycoside contents naturally occurring in the fruit. In some variations, the clarified juice is contacted with the adsorbent medium to produce an effluent having an amount of mogroside V that is two times less, three times less, or four times less than the amount of mogroside V naturally occurring in the fruit. In another variation, the clarified juice is contacted with the adsorbent medium to produce an effluent having an amount of mogroside V that is between two to three times less, three to four times less, or two to four times less than the amount of mogroside V naturally occurring in the fruit. In yet other variations, the clarified juice is contacted with the adsorbent medium to produce an effluent having an amount of mogroside V that is at least about 95%, at least about 96%, at least about 97%, or at least about 98% less than the amount of mogroside V naturally occurring in the fruit. In certain variations, the clarified juice is contacted with the adsorbent medium to produce an effluent having an amount of mogroside V that is between about 95% to about 98%, between about 95% to about 97%, between about 95% to about 96%, between about 96% to about 98%, between 96% to 97%, or between 97% to 98% less than the amount of mogroside V naturally occurring in the fruit. The effluent obtained from contact with the adsorbent medium may further comprise monosaccharides, disaccharides, polysaccharides, proteins, fruit acids, and minerals.

In some variations, the effluent is contacted with the nanofiltration membrane to produce a retentate having an amount of monosaccharides that is two times less, three times less, or four times less than the amount of monosaccharides in the effluent. In another variation, the effluent is contacted with the nanofiltration membrane to produce a retentate having an amount of monosaccharides that is between two to three times less, three to four times less, or two to four times less than the amount of monosaccharides in the effluent.

In other variations, the retentate obtained from the nanofiltration step has a lower monosaccharide content than the monosaccharide content naturally occurring in the fruit. In some variations, the retentate has an amount of monosaccharides that is two times less, three times less, or four times less than the amount of monosaccharides naturally occurring in the fruit. In another variation, the retentate has an amount of monosaccharides that is between two to three times less, three to four times less, or two to four times less than the amount of monosaccharides naturally occurring in the fruit.

In certain embodiments, the extract is produced from a mogroside-depleted luo han guo juice. In some variations, the mogroside-depleted luo han guo juice is prepared by contacting luo han guo with water to produce a water-extracted juice, and contacting the water-extracted juice with an adsorbent medium to remove at least a portion of mogroside V and other terpene glycosides in the water-extracted juice. The effluent that comes from contact with the adsorbent medium is a mogroside-depleted luo han guo juice. In some variations of the foregoing, the water-extracted juice may be clarified prior to contact with the adsorbent medium.

A mogroside-depleted luo han guo juice has a lower mogroside V content as compared to the juice extracted from the fruit. In some variations, a mogroside-depleted luo han guo juice has a substantially lower mogroside V content as compared to the juice extracted from the fruit. It should be understood, however, that mogroside V is present in mogroside-depleted luo han guo juice, and such mogroside-depleted luo han guo juice may be used to prepare the extracts described herein having a low mogroside V content.

In other embodiments, provided is a method for producing the extract that comprises extracting a juice from luo han guo, contacting the extracted juice with a nanofiltration membrane to lower the monosaccharide content, and then contacting the filtered juice with an adsorbent medium to lower the mogroside V content. In such an embodiment, the extracted juice is contacted with the adsorbent medium after the nanofiltration step.

The various steps of the methods for producing the extract, along with the nanofiltration membrane and adsorbent medium, are described in further detail below.

Extraction

Juice from the fruit of the Cucurbitaceae family may be extracted by contacting macerated fruit with hot water, or water at elevated temperatures. In certain embodiments, the macerated fruit is contacted with water for a sufficient time and at a sufficient temperature to obtain the water-extracted juice.

In some embodiments, the fruit is contacted with water at a temperature of at least 60° C., at least 70° C., or at least 80° C. In other embodiments that may be combined with the foregoing, the fruit is contacted with water for between 30 to 60 minutes, or between 90 to 120 minutes.

In some variations of the foregoing, this extraction step is carried out using countercurrent extraction.

Clarification

The water-extracted juice may be clarified prior to contact with the nanofiltration membrane. In some embodiments, the clarifying step comprises ultrafiltering the water-extracted juice. In certain embodiments, the clarifying step comprises treating the extract with a pectinase enzyme under conditions which lyse pectins and complex saccharides.

Adsorbent Medium

The adsorbent medium used in the methods described herein may be a single medium or a mixture of suitable media.

In some embodiments, the adsorbent medium is an adsorbent resin. In one variation, the adsorbent resin is provided as a bed of adsorbent resin. In embodiments where the adsorbent material is an adsorbent resin, suitable adsorbent resins may include any resins with a wettable hydrophobic matrix that are suitable for contact with food, including, for example, polyvinlpolypyrrolidone (PVPP), nylon, acrylic esters, styrene divinylbenzene copolymers, and divinylbenzene copolymers. In some variations, the adsorbent resin is a macroporous polymeric adsorbent resin. In certain variations, the adsorbent resin is a styrenyl copolymer resin. In other variations, the adsorbent resin is a styrene divinylbenzene copolymer or a divinylbenzene copolymer. Any combinations of media described herein may also be used.

The adsorbent medium used in the methods described may be obtained from any commercially available source or produced according to any methods or techniques known in the art.

Nanofiltration Membrane

In some embodiments, the nanofiltration membranes selectively remove at least a portion of the monosaccharides in the water-extracted juice or the mogroside-depleted juice. In some variations, the nanofiltration membrane used in the methods described herein has a molecular weight cutoff between 100 Daltons and 5,000 Daltons, between 100 Daltons and 2,500 Daltons, between 100 Daltons and 2,000 Daltons, between 200 Daltons and 2,500 Daltons, between 200 Daltons and 2,000 Daltons, between 500 Daltons and 2,500 Daltons, between 500 Daltons and 2,000 Daltons, or between 500 Daltons and 1,000 Daltons.

The nanofiltration membrane may be obtained from a commercially available source.

When a water-extracted juice or a mogroside-depleted juice is contacted with the nanofiltration membrane, a retentate and a permeate are generated. The retentate comprises components that are unable to pass through the nanofiltration membrane. The permeate comprises components, such as monosaccharides, that are able to pass through the membrane based on the molecular weight cutoff of the membrane.

In some variations, the soluble solids content of the retentate is monitored. Water may be added to the retentate, the diluted retentate is contacted with the nanofiltration membrane, and this process is repeated. For example, the process may be repeated until the retentate achieves a low level of monosaccharides and/or the retentate has no sour taste.

In some embodiments, soluble solids in the retentate may include monosaccharides, disaccharides, polysaccharides, inorganic salts, minerals, or proteins, or any combinations thereof. Soluble solids content may be measured using any suitable methods and techniques known in the art. For example, soluble solids content may be measured using a brix refractometer. Soluble solids content may be expressed in any appropriate units. For example, the soluble solids content may be expressed as a weight ratio (g of soluble solids/g of sample), as a percentage (% w/w) on a dry weight basis, or as degrees Brix.

In certain embodiments, provided is a method for producing a spray-dried extract derived from a fruit of the Cucurbitaceae family, the method comprising:

a) providing a mogroside-depleted juice obtained from the fruit;

b) filtering the mogroside-depleted juice using a nanofiltration membrane to produce a retentate, wherein the nanofiltration membrane has a molecular weight cutoff between 250 Daltons and 2,500 Daltons;

c) monitoring the soluble solids concentration of the retentate of step (b);

d) diluting the retentate of step (c) with water, when the soluble solids concentration of the retentate of step (c) is about 5 g/100 g, to produce a diluted retentate;

e) filtering the diluted retentate using the nanofiltration membrane to produce another retentate;

f) monitoring the soluble solids concentration of the retentate of step (e);

g) diluting the retentate of step (e) with water to produce another diluted retentate;

h) repeating steps (e) through (g) until the monosaccharide concentration of the retentate is less than about 20% on a dry weight basis or until no sour taste is observed from the retentate;

i) after step (h), concentrating the retentate to produce a concentrated retentate having a soluble solids concentration of about 20 g/100 g; and j) spray drying the concentrated retentate to produce a spray-dried extract.

In one variation of the foregoing, the mogroside-depleted juice is obtained by contacting juice extracted from the fruit with an adsorbent resin whereby at least a portion of the mogroside V in the extracted juice binds to the adsorbent resin.

In another embodiment, provided is a method for producing a spray-dried extract derived from a fruit of the Cucurbitaceae family, the method comprising:

a) filtering a water-extracted juice obtained from the fruit using a nanofiltration membrane to produce a retentate, wherein the nanofiltration membrane has a molecular weight cutoff between 250 and 2,500 Daltons;

b) monitoring the soluble solids concentration of the retentate of step (a);

c) diluting the retentate of step (b) with water, when the soluble solids concentration of the retentate of step (b) is about 5 g/100 g, to produce a diluted retentate;

d) filtering the diluted retentate using the nanofiltration membrane to produce another retentate;

e) monitoring the soluble solids concentration of the retentate of step (d);

f) diluting the retentate of step (d) with water to produce another diluted retentate;

g) repeating steps (d) through (f) until the monosaccharide concentration of the retentate is less than about 20% on a dry weight basis or until no sour taste is observed from the retentate;

h) after step (g), contacting the retentate with an adsorbent resin, wherein the resin binds terpene glycosides and mogroside V, and collecting the mogroside-depleted effluent; and i) concentrating and spray drying the effluent to produce a spray-dried extract.

The retentate may contain fruit acids that are naturally present in the fruit. Thus, a total acid content and pH may be determined for the retentate. In certain embodiments, the concentrated retentate has a total acid content less than about 5% w/w, less than about 3% w/w, or less than about 2.5% w/w. In other embodiments, the concentrated retentate has a pH of greater than pH of about 4. In certain embodiments, the concentrated retentate has a pH greater than or equal to pH of between 4 and 4.5.

The retentate may contain monosaccharides, disaccharides and polysaccharides. In some variations, the retentate has a total sugar content less than or equal to the total sugar content in the mogroside-depleted juice or the water-extracted juice.

Provided herein are also extracts produced according to any of the methods described herein.

Sweetening Compositions

The extracts described herein may be used as a bulking agent, and combined with another sweetening extract to produce a sweetening composition. For example, the extracts described herein may be combined with a concentrated terpene glycoside extract that is also derived from fruit of the Cucurbitaceae family to prepare a sweetening composition.

In some aspects, provided is a sweetening composition comprising a bulking agent extract as described herein or produced according to the methods herein, and a concentrated terpene glycoside extract also obtained from luo han guo.

In certain variations, the extracts described herein are used as a bulking agent in a sweetening composition whose components are all naturally occurring in the fruit from which the sweetening composition was obtained. For example, in one variation, the bulking agent extract is derived from luo han guo, according to any of the methods described herein, and is combined with a terpene glycoside extract also derived from luo han guo. In such a variation, all components of the sweetening composition are naturally occurring in the fruit from which the sweetening composition was obtained.

In some variations, at least 95%, at least 96%, at least 97%, at least 98%, at least 99%, at least 99.5%, or at least 99.9% of the components in the sweetening composition, on a dry weight basis, is naturally occurring (or naturally present) in luo han guo from which the extract was obtained. In certain variations, all components of the sweetening composition are naturally occurring (or naturally present) in luo han guo from which the extract was obtained. Thus, in certain variations, the sweetening composition is a natural luo han guo sweetening composition. In one variation, a natural luo han guo sweetening composition may include less than 5% on a dry weight basis of an incidental additive or processing aid that is not naturally occurring (or naturally present) in luo han guo. In one variation, a natural luo han guo sweetening composition may include a trace amount or less than 0.01% on a dry weight basis of a non-naturally occurring component.

In some embodiments of the sweetening composition, the ratio of the bulking agent extract to the terpene glycoside extract in the sweetening composition may be adjusted such that 1 g of sweetening composition is equivalent in sweetness to 4 g of table sugar. It is understood that this ratio may depend upon the mogroside V content of the bulking agent extract and the terpene glycoside extract.

In other aspects, provided is a food, beverage, or dietary supplement comprising any of the sweetening compositions described herein. Provided also is the use of such a sweetening composition described herein in a food, beverage or dietary supplement.

In variations where a spray-dried extract is combined with a solid terpene glycoside extract, the sweetening composition is in solid form. In one variation, the sweetening composition is provided in tablet form. In other variations, the sweetening composition is provided as powder in a packet or sachet.

Method of Producing the Sweetening Composition

In other aspects, provided herein is a method for producing a sweetening composition that comprises: an extract produced according to the methods described herein, suitable for use as a bulking agent; and a terpene glycoside extract.

Figure 2:
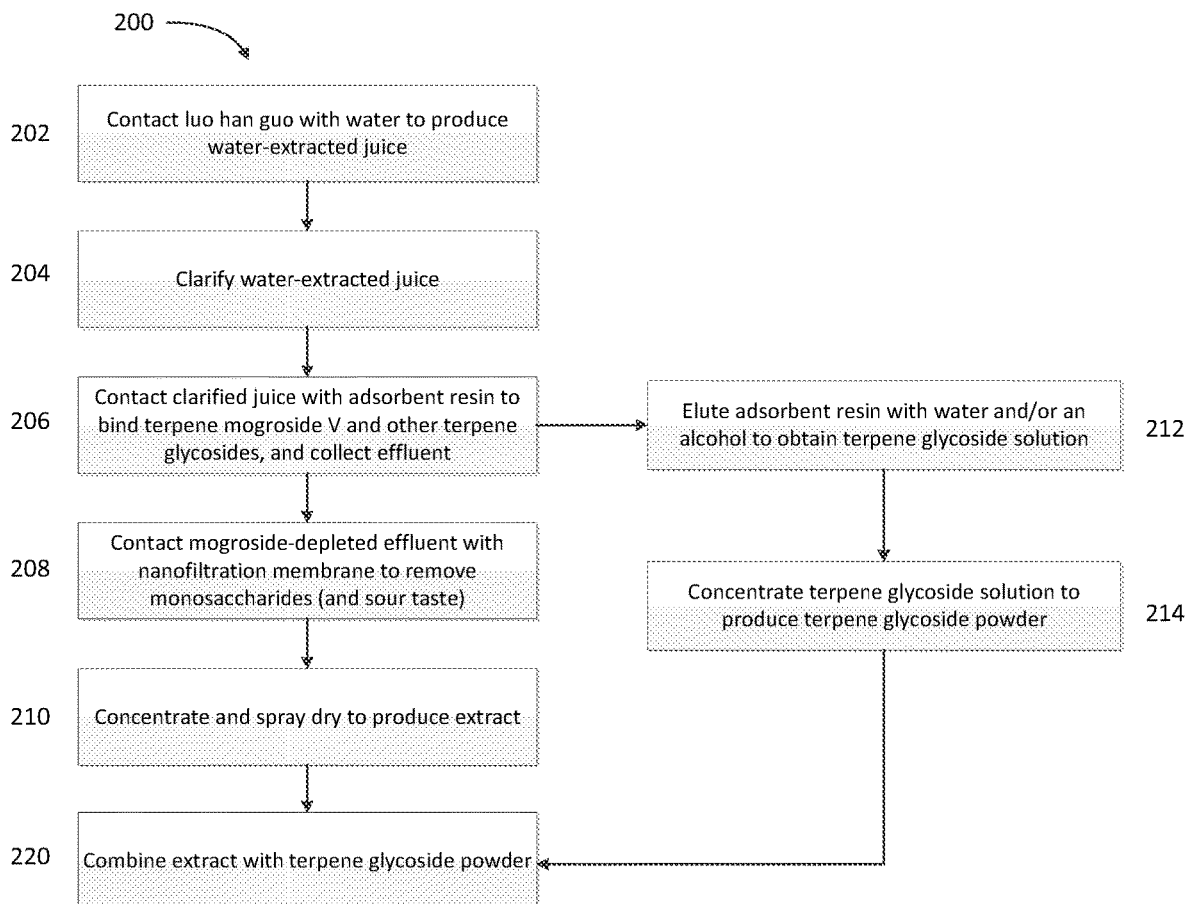
FIG. 2 depicts an exemplary process to prepare a sweetening composition derived from luo han guo.

With reference to FIG. 2, process 200 depicts an exemplary process to prepare a sweetening composition from luo han guo, that comprises a terpene glycoside powder and a spray-dried extract having a low mogroside V content suitable for use as a bulking agent in the composition. In process 200, both the spray-dried extract and the terpene glycoside powder are obtained from the same fruit.

In step 202, the fruit is contacted with water to produce a water-extracted juice. The water-extracted juice comprises mogroside V, other terpene glycosides and monosaccharides. The water-extracted juice is clarified in step 204 (e.g., to remove pectin and other proteins), thereby facilitating subsequent processing. In step 206, the clarified juice is contacted with an adsorbent resin, wherein at least a portion of the mogroside V and other terpene glycosides in the clarified juice are adsorbed onto the resin.

The effluent that comes off the adsorbent resin is a mogroside-depleted effluent, and is contacted with a nanofiltration membrane in step 208. At least a portion of small molecules, including monosaccharides and fruit acids, are removed in step 208. In step 210, the retentate produced from the nanofiltration step is concentrated and spray-dried to produce an extract. Such extract from step 210 is suitable for use as a bulking agent in the sweetening composition produced in process 200.

In step 212, the adsorbed mogroside V and other terpene glycosides are eluted from the resin with water and/or an alcohol to obtain a terpene glycoside solution. Suitable alcohols to elute the resin may include, for example, ethanol. In step 214, the terpene glycoside solution is concentrated to produce a terpene glycoside powder.

In step 220, the spray-dried extract of step 210 is combined with the terpene glycoside powder of step 214 to produce a sweetening composition. All components of the sweetening composition produced according to process 200 are naturally from the fruit used.

In some embodiments, provided is a method for producing a sweetening composition derived from a fruit of the Cucurbitaceae family, the method comprising:

a) providing a water-extracted juice, wherein the water-extract juice comprises mogroside V, other terpene glycosides, and monosaccharides;

b) clarifying the water-extracted juice;

c) contacting the clarified juice with an adsorbent medium to adsorb at least a portion of mogroside V and other terpene glycosides in the clarified juice and to produce an effluent;

d) filtering the effluent using a nanofiltration membrane to remove at least a portion of the monosaccharides in the effluent and to produce a retentate;

e) concentrating the retentate and spray drying the retentate to produce an extract;

f) eluting the adsorbent resin after step (c) to elute at least a portion of the adsorbed mogroside V and other terpene glycosides to obtain a terpene glycoside solution;

g) drying the terpene glycoside solution to produce a terpene glycoside powder; and h) combining the extract of step (e) and the terpene glycoside powder of step (g) to produce the sweetening composition.

In another variation, provided is a method of producing a luo han guo sweetening composition, comprising:

a) heating fresh luo han guo in water to obtain a water-extracted juice, wherein the water-extracted juice comprises mogroside V and other terpene glycosides;

b) clarifying the water-extracted juice, wherein the clarified juice comprises mogroside V and other terpene glycosides;

c) contacting the clarified juice with an absorbent resin, wherein at least a portion of the mogroside V and other terpene glycosides in the clarified juices binds to the adsorbent resin to produce a mogroside-depleted juice;

d) after step c), eluting the mogroside V and other terpene glycosides from the adsorbent resin to obtain a terpene glycoside solution;

e) drying the terpene glycoside solution to produce a terpene glycoside powder;

f) filtering the mogroside-depleted juice using a nanofiltration membrane to produce a retentate, wherein the nanofiltration membrane has a molecular weight cut-off between 200 Daltons and 2,500 Daltons;

g) monitoring the soluble solids concentration of the retentate of step (f);

h) diluting the retentate of step (f) with water, when the soluble solids concentration of the retentate of step (f) is about 5 g/100 g, to produce a diluted retentate;

i) filtering the diluted retentate using the nanofiltration membrane to produce another retentate;

j) monitoring the soluble solids concentration of the retentate of step (i);

k) diluting the retentate of step (i) with water to produce another diluted retentate;

l) repeating steps (f)-(k) until the monosaccharide concentration of the retentate of step (i) is about 20% on a dry weight basis;

m) after step (l), concentrating the retentate to produce a concentrated retentate having a soluble solids concentration of about 20 g/100 g;

n) spray drying the concentrated retentate to produce the spray-dried extract; and o) combining the terpene glycoside powder and the spray-dried extract to produce the sweetening composition, wherein the sweetening composition is in solid form.

With reference again to FIG. 2, it should be understood that, in other variations, process 200 may include additional and/or other processing steps. In yet other variations, certain steps in process 200 may be omitted. For example, as an alternative to combining the terpene glycoside powder with the spray-dried extract, in other variations, the concentrated retentate and the terpene glycoside solution can be combined, and then spray-dried to produce the extract.

In another variation, provided is a method of producing a luo han guo sweetening composition, comprising:

a) heating fresh luo han guo in water to obtain a water-extracted juice, wherein the water-extracted juice comprises mogroside V and other terpene glycosides;

b) clarifying the water-extracted juice, wherein the clarified juice comprises mogroside V and other terpene glycosides;

c) contacting the clarified juice with an absorbent resin, wherein at least a portion of the mogroside V and other terpene glycosides in the clarified juices binds to the adsorbent resin to produce a mogroside-depleted juice;

d) after step c), eluting the mogroside V and other terpene glycosides from the adsorbent resin to obtain a terpene glycoside solution;

e) drying the terpene glycoside solution to produce a terpene glycoside powder;

f) filtering the mogroside-depleted juice using a nanofiltration membrane to produce a retentate, wherein the nanofiltration membrane has a molecular weight cut-off between 200 and 2,500 Daltons;

g) monitoring the soluble solids concentration of the retentate of step (f);

h) diluting the retentate of step (f) with water, when the soluble solids concentration of the retentate of step (f) is about 5 g/100 g, to produce a diluted retentate;

i) filtering the diluted retentate using the nanofiltration membrane to produce another retentate;

j) monitoring the soluble solids concentration of the retentate of step (i);

k) diluting the retentate of step (i) with water to produce another diluted retentate;

l) repeating steps (f)-(k) until the monosaccharide concentration of the retentate of step (i) is about 20% on a dry weight basis;

m) after step (l), concentrating the retentate to produce a concentrated retentate having a soluble solids concentration of about 20 g/100 g;

n) combining the concentrated retentate of step (m) with the terpene glycoside powder of step (e); and o) spray drying the combined concentrated retentate and terpene glycoside powder to produce the luo han guo sweetening composition.

In some variations of the foregoing embodiments, the adsorbent resin is eluted with water, an alcohol, or a mixture thereof. In one variation, the alcohol comprises ethanol.

Any of the nanofiltration membranes described herein may be used. For example, in certain variations, the nanofiltration membrane has molecular weight cutoff between 200 Daltons and 2,500 Daltons.

In some variations, the terpene glycoside powder comprises at least 30% w/w mogroside V. In other variations, the terpene glycoside powder comprises between 30% to 60% w/w mogroside V.

Provided is also a sweetening composition derived from a fruit of the Cucurbitaceae family, produced according to any of the methods described herein.

It should be understood that reference to "about" a value or parameter herein includes (and describes) embodiments that are directed to that value or parameter per se. For example, description referring to "about x" includes description of "x" per se. In other instances, the term "about" when used in association with other measurements, or used to modify a value, a unit, a constant, or a range of values. In some embodiments, about refers to variations of +/−20%. In other embodiments, about refers to variations of +/−15%. In one embodiment, about refers to variations of +/−10%. In one variation, about refers to variations of +/−5%. In another variation, about refers to variations of +/−1%.

EXAMPLES

The following Examples are merely illustrative and are not meant to limit any aspects of the present disclosure in any way.

Example 1

Production of Extract from Luo Han Guo

This Example describes the production of an extract from luo han guo. Such extract has a low mogroside V content. and a low monosaccharide content, and is suitable for spray drying to produce an extract in a spray-dried powdered form.

Fresh luo han guo is mechanically shredded and dropped into a steam jacketed vat. Filtered water is added to the macerated fruit. The water is heated to 100° C. and the mixture is decocted for 45 minutes. After 45 minutes, the decoction is drained off the fruit, and filtered to remove large fruit particles. Additional water is added to the fruit remaining in the vat. The water is heated to 100° C. and the mixture is decocted for 45 minutes. After 45 minutes, the decoction is drained off the fruit, filtered to remove large fruit particles, and combined with the decoction from the first cycle. This cycle may be repeated.

Suspended solids are then removed, to avert blinding of adsorbent resin. A pectinase enzyme preparation is added, and the mixture is gently stirred for 30 minutes until a flock forms and begin to settle. Then, the temperature is increased to 85° C. to terminate the enzyme activity, and the temperature is held at 85° C. for an additional 5 minutes to denature labile indigenous fruit proteins. Thereafter, the separating mixture is cooled (e.g., to less than 50° C.) for ease of filtration through diatomaceous earth under vacuum.

Next, the extract is contacted with a commercially available divinylbenzene copolymer adsorbent resin packed in a glass chromatography column. The extract is allowed to percolate through the resin at ambient temperature. A mogroside-depleted juice passes out of the column, and is made up of fruit sugars, acids and minerals.

This mogroside-depleted juice is collected and filtered using a nanofiltration membrane, having a molecular weight cutoff between 250 Daltons and 2,500 Daltons. The soluble solids in the retentate of this filtration step are monitored. When the soluble solids content reaches 5 g/100 g, the retentate is diluted with purified water. This process is repeated until the retentate has no sour taste.

Nanofiltration is then continued until the soluble solids content in the retentate reaches 10 g/100 g.

The retentate is then collected and evaporated until the soluble solids content in the retentate reaches 20 g/100 g. The concentrated retentate is then spray dried.

Example 2

Spray Drying Experiment

In this Example, various retentates from a nanofiltration process were spray dried. Juice was extracted from luo han guo, and underwent processing including contact with an adsorbent resin to produce a mogroside-depleted juice.

Experiment 1

A 4000 L of mogroside-depleted juice with a soluble solid content of 1.1% Brix was filtered using a nanofiltration membrane with a molecular weight cut-off of about 500 Daltons. The pressure used was maintained at 0.5 MPa. After 3 h, the soluble solid content of the retentate was 5.7% Brix, and of the permeate was 1.2% Brix. The filtration was then stopped, and 500 L of water was added to the tank holding retentate. Filtration was continued on the diluted retentate under a pressure of 0.8 MPa. After 20 min, the soluble solid content of the retentate was 6.3% Brix and the permeate was 0.7% Brix. The filtration was stopped, and 400 L of water was added to the tank holding the retentate. The filtration process was repeated. After 20 min, the soluble solid content of the retentate about 5.6% Brix and the permeate was 0.4% Brix. About 2 L of the retentate was then collected (retentate 1).

After the retentate sample was collected, water (300 L×2) was added for dilution, followed by filtration. After 40 min, the soluble solid content of the retentate was 7.3% Brix and the permeate was 0.4% Brix. About 2 L of the retentate was collected (retentate 2).

Retentates 1 and 2 above were concentrated with reduced pressure through rotary evaporator until the soluble solid content was around 35% Brix. Then, spray-drying was performed at a wind-in temperature of 149-159° C. and wind-out temperature of 79-85° C.

The mogroside V content, sugar content, acid content, pH value and absorbance value of the spray-dried products were measured.

Experiment 2

A 3000 L of mogroside-depleted juice with a soluble solid content of 5.5% Brix was filtered using a nanofiltration membrane with a molecular weight cut-off of about 500 Daltons. The pressure used was maintained at 0.9 MPa. After 1.5 h, the soluble solid content of the retentate was 8.2% Brix, and of the permeate was 2.7% Brix. The filtration was then stopped, and 550 L of water was added to the tank holding retentate. Filtration was continued on the diluted retentate under a pressure of 0.9 MPa. After 1.5 h, the soluble solid content of the retentate was 9.0% Brix and the permeate was 1.4% Brix. The filtration was stopped, and 500 L of water was added to the tank holding the retentate. The filtration process was repeated. After 20 min, the soluble solid content of the retentate about 6.5% Brix and the permeate was 0.6% Brix. About 2 L of the retentate was then collected (retentate 1).

After the retentate sample was collected, water (300 L×2) was added for dilution, followed by filtration. After 40 min, the soluble solid content of the retentate was 7.5% Brix and the permeate was 0.5% Brix. About 2 L of the retentate was collected (retentate 2).

Retentates 1 and 2 above were concentrated with reduced pressure through rotary evaporator until the soluble solid content was around 35% Brix. Then, spray-drying was performed at a wind-in temperature of 149-159° C. and wind-out temperature of 79-85° C.

The mogroside V content, sugar content, acid content, pH value and absorbance value of the spray-dried products were measured.

Experiment 3

A 500 L of mogroside-depleted juice with a soluble solid content of 1.1% Brix was filtered using a nanofiltration membrane with a molecular weight cut-off of about 500 Daltons. The mogroside-depleted juice in this experiment was concentrated under reduced pressure. This juice was diluted with 400 L of water, and the pressure for the nanofiltration was maintained at 0.9 MPa. After 45 mins, the soluble solid content of the retentate was 8.6% Brix, and of the permeate was 1.9% Brix. The filtration was then stopped, and about 2 L of the retentate was then collected (retentate 1).

150 L of water was added to the tank holding the retentate. Filtration was continued on the diluted retentate under a pressure of 0.9 MPa. After 0.5 h, the soluble solid content of the retentate was 7.6% Brix and of the permeate was 1.1% Brix. Filtration was stopped, and about 2 L of the retentate was then collected (retentate 2).

150 L of water was added to the tank holding the retentate. Filtration was then continued. After 20 mins, the soluble solid content of the retentate was 7.6% Brix, and of the permeate was 0.6% Brix. About 2 L of the retentate was collected (retentate 3).

400 L of water was added to the tank holding the retentate. Filtration was the continued. After 40 mins, the soluble solid content of the retentate was 7.6% Brix, and of the permeate was 0.6% Brix. About 2 L of the retentate was collected (retentate 4).

400 L of water was added to the tank holding the retentate. Filtration was the continued. After 20 mins, the soluble solid content of the retentate was 6.5% Brix, and of the permeate was 0.2% Brix. About 2 L of the retentate was collected (retentate 5).

Retentates 1-5 above were concentrated with reduced pressure through rotary evaporator until the soluble solid content was around 35% Brix. Then, spray-drying was performed at a wind-in temperature of 149-159° C. and wind-out temperature of 79-85° C.

The mogroside V content, sugar content, acid content, pH value and absorbance value of the spray-dried products were measured.

Results

Table 1 below summarizes the properties of the various retentate samples.

During the nanofiltration process, the density of the retentate is maintained at a certain level, and in order to do so, washing water was continuously added to the retentate to maintain its density. Thus, the amount of washing water used (or the "washing water consumption" in Table 1 below) increased over time during the nanofiltration process, and the amount of washing water shown in the table is a proxy for time in the nanofiltration process.

In Experiment 1, after 700 L of washing water consumption, a spray-dried extract was obtained, but some sticking to the inside of the spray drier was observed. A spray-dried extract was obtained after 1100 L of washing water consumption.

In Experiment 2, after 2500 L of washing water consumption, a spray-dried extract was obtained, but some sticking to the inside of the spray drier was observed. A spray-dried extract was obtained after 3500 L of washing water consumption.

In Experiment 3, after 900 L of washing water consumption, a spray-dried extract was obtained, but some sticking to the inside of the spray drier was observed. A spray-dried extract was obtained after 1500 L of washing water consumption.

What is claimed is:

1. A method of producing a spray-dried extract, comprising:
   a) filtering a mogroside-depleted luo han guo juice using a nanofiltration membrane to produce a retentate, wherein the nanofiltration membrane has a molecular weight cut-off between 200 Daltons and 2,500 Daltons;
   b) monitoring the soluble solids concentration of the retentate of step (a);
   c) diluting the retentate of step (a) with water, when the soluble solids concentration of the retentate of step (a) is about 5 g/100 g, to produce a diluted retentate;
   d) filtering the diluted retentate using the nanofiltration membrane to produce filtered retentate;
   e) monitoring the soluble solids concentration of the filtered retentate of step (d);
   f) diluting the filtered retentate of step (d) with water to produce another diluted retentate;
   g) repeating steps (d)-(f) until the monosaccharide concentration of the filtered retentate of step (d) is less than about 20% on a dry weight basis and mogroside V concentration of the filtered retentate of step (d) is less than about 2% on a dry weight basis, wherein the mogroside V is naturally occurring in luo han guo from which the mogroside-depleted luo han guo juice was obtained;
   h) after step (g), concentrating the retentate to produce a concentrated retentate having a soluble solids concentration of about 20 g/100 g; and
   i) spray drying the concentrated retentate to produce the spray-dried extract.

2. The method of claim 1, wherein the retentate has less than about 1% mogroside V on a dry weight basis.

3. The method of claim 1, wherein the retentate of step (g) comprises monosaccharides,
   wherein the monosaccharides are naturally occurring in luo han guo from which the mogroside-depleted luo han guo juice was obtained, and
   wherein the retentate has less than about 20% monosaccharides on a dry weight basis.

4. The method of claim 1, wherein the retentate of step (g) further comprises disaccharides and polysaccharides,
   wherein the disaccharides and polysaccharides are naturally occurring in luo han guo from which the mogroside-depleted luo han guo juice was obtained, and
   wherein the retentate has a total sugar content of less than or equal to about 20% on a dry weight basis.

TABLE 1

| Expt No. | Volume L | Soluble solids content g/100 g | Solid weight Kg | Washing water consumption L | pH | Total acids % | Mono- saccharides % | Total sugars % | Absorbance (1%, at 420 nm) | Mogroside V % |
|---|---|---|---|---|---|---|---|---|---|---|
| 1 | 500 | 8.5 | 42.5 | 0 | 3.86 | 8.45 | 29.2 | | 0.224 | 0.28 |
| | | | | 400 | 4 | 5.76 | 22.7 | | 0.294 | 0.33 |
| | | | | 550 | 4.14 | 3.84 | 18.1 | | 0.36 | 0.43 |
| | | | | 700 | 4.27 | 3.07 | 13.7 | | 0.441 | 0.48 |
| | | | | 1100 | 4.44 | 2.50 | 10.8 | | 0.413 | 0.53 |
| | | | | 1500 | 4.48 | 2.16 | 9.9 | | 0.42 | 0.56 |
| 2 | 3000 | 5.5 | 165 | 0 | 4.26 | 10.55 | 57.0 | 70.5 | 0.065 | 0.13 |
| | | | | 950 | 4.41 | 3.00 | 41.3 | 63.5 | 0.071 | 0.26 |
| | | | | 2500 | 4.62 | 2.30 | 13.6 | 62.7 | 0.091 | 0.3 |
| | | | | 3500 | 4.61 | 2.20 | 10.3 | 58.7 | 0.103 | 0.46 |
| 3 | 4000 | 1.1 | 44 | 0 | 3.86 | 8.90 | 25.3 | 65.9 | 0.266 | 0.23 |
| | | | | 900 | 4.42 | 3.00 | 13.3 | 61.3 | 0.445 | 0.65 |
| | | | | 1500 | 4.57 | 2.50 | 8.0 | 46.3 | 0.7 | 1.03 |

5. The method of claim 1, wherein the mogroside-depleted luo han guo juice is obtained by:
heating fresh luo han guo in water to obtain a water-extracted juice, wherein the water-extracted juice comprises mogroside V;
clarifying the water-extracted juice, wherein the clarified juice comprises mogroside V; and
contacting the clarified juice with an absorbent resin, wherein at least a portion of the mogroside V in the clarified juice binds to the adsorbent resin thereby reducing the concentration of mogroside V in the clarified juice.

6. A spray-dried extract produced according to the method of claim 1.

7. A method of producing a luo han guo sweetening composition, comprising:
a) heating fresh luo han guo in water to obtain a water-extracted juice, wherein the water-extracted juice comprises mogroside V and other terpene glycosides;
b) clarifying the water-extracted juice, wherein the clarified juice comprises mogroside V and other terpene glycosides;
c) contacting the clarified juice with an absorbent resin, wherein at least a portion of the mogroside V and other terpene glycosides in the clarified juices binds to the adsorbent resin to produce a mogroside-depleted juice;
d) after step c), eluting the mogroside V and other terpene glycosides from the adsorbent resin to obtain a terpene glycoside solution;
e) drying the terpene glycoside solution to produce a terpene glycoside powder;
filtering the mogroside-depleted juice using a nanofiltration membrane to produce a retentate, wherein the nanofiltration membrane has a molecular weight cut-off between 200 and 2,500 Daltons;
g) monitoring the soluble solids concentration of the retentate of step (f);
h) diluting the retentate of step (f) with water, when the soluble solids concentration of the retentate of step (f) is about 5 g/100 g, to produce a diluted retentate;
i) filtering the diluted retentate using the nanofiltration membrane to produce filtered retentate;
j) monitoring the soluble solids concentration of the filtered retentate of step (i);
k) diluting the filtered retentate of step (i) with water to produce another diluted retentate;
l) repeating steps (f)-(k) until the monosaccharide concentration of the filtered retentate of step (i) is about 20% on a dry weight basis and mogroside V concentration of the filtered retentate of step (i) is less than about 2% on a dry weight basis;
m) after step (1), concentrating the retentate to produce a concentrated retentate having a soluble solids concentration of about 20 g/100 g;
n) spray drying the concentrated retentate to produce the spray-dried extract; and
o) combining the terpene glycoside powder and the spray-dried extract to produce the sweetening composition, wherein the sweetening composition is in solid form.

8. A method of producing a luo han guo sweetening composition, comprising:
a) heating fresh luo han guo in water to obtain a water-extracted juice, wherein the water-extracted juice comprises mogroside V and other terpene glycosides;
b) clarifying the water-extracted juice, wherein the clarified juice comprises mogroside V and other terpene glycosides;
c) contacting the clarified juice with an absorbent resin, wherein at least a portion of the mogroside V and other terpene glycosides in the clarified juices binds to the adsorbent resin to produce a mogroside-depleted juice;
d) after step c), eluting the mogroside V and other terpene glycosides from the adsorbent resin to obtain a terpene glycoside solution;
e) drying the terpene glycoside solution to produce a terpene glycoside powder;
f) filtering the mogroside-depleted juice using a nanofiltration membrane to produce a retentate, wherein the nanofiltration membrane has a molecular weight cut-off between 200 and 2,500 Daltons;
g) monitoring the soluble solids concentration of the retentate of step (f);
h) diluting the retentate of step (f) with water, when the soluble solids concentration of the retentate of step (f) is about 5 g/100 g, to produce a diluted retentate;
i) filtering the diluted retentate using the nanofiltration membrane to produce filtered retentate;
j) monitoring the soluble solids concentration of the filtered retentate of step (i);
k) diluting the filtered retentate of step (i) with water to produce another diluted retentate;
l) repeating steps (f)-(k) until the monosaccharide concentration of the filtered retentate of step (i) is about 20% on a dry weight basis and mogroside V concentration of the filtered retentate of step (i) is less than about 2% on a dry weight basis;
m) after step (1), concentrating the retentate to produce a concentrated retentate having a soluble solids concentration of about 20 g/100 g;
n) combining the concentrated retentate of step (m) with the terpene glycoside powder of step (e); and
o) spray drying the combined concentrated retentate and terpene glycoside powder to produce the luo han guo sweetening composition.

9. The method of claim 7, further comprising compressing the sweetening composition to form a tablet.

10. A luo han guo sweetening composition produced according to the method of claim 7.

* * * * *